US006429225B1

(12) United States Patent
Nagai et al.

(10) Patent No.: US 6,429,225 B1
(45) Date of Patent: Aug. 6, 2002

(54) **CHELATE COMPOUND-CONTAINING ANTIBACTERIAL AGENT FOR *HELICOBACTER PYLORI***

(75) Inventors: Toshiro Nagai, Tsukuba; Shigeru Oita, Zentsuji, both of (JP)

(73) Assignees: Director of National Institute of Agrobiological Resources, Ministry of Agriculture, Forestry and Fisheries; National Agricultural Research Organization, both of Tsukuba (JP)

( * ) Notice: Subject to any disclaimer, the term of this patent is extended or adjusted under 35 U.S.C. 154(b) by 0 days.

(21) Appl. No.: 09/802,270

(22) Filed: Mar. 8, 2001

(30) Foreign Application Priority Data

Nov. 16, 2000 (JP) ....................................... 2000-349003

(51) Int. Cl.$^{7}$ ............................................. A61K 31/295

(52) U.S. Cl. ........................ 514/502; 514/566; 514/925

(58) Field of Search ................................. 514/502, 566

(56) References Cited

PUBLICATIONS

DATABASE PubMed, Whittaker et al, Regul. Toxicol. Pharmacol , Dec. 1993, 18(3), 419–27, abstract.*

MEDLINE 86242415, Cardan et al, Arzneimittle–forschunhg, Apr. 1986, 36(4), 756–8, abstract.*

BIOSUS PREV199497124372, Perez–Perez et al, Infection and Immunity, 1994, 62(1), 299–302, abstract.*

Y. Koga and A. Takagi, "Anti–*Helicobacter pylori* Activity of a Lactic Acid Bacillus", *Shokunokagaku*, 265, 87–89 (2000).

* cited by examiner

*Primary Examiner*—Rebecca Cook
(74) *Attorney, Agent, or Firm*—Frishauf, Holtz, Goodman & Chick, P.C.

(57) ABSTRACT

An antibacterial agent is provided, which has an action for inhibiting growth of *Helicobacter pylori* participating to occurrence of chronic gastritis and gastric ulcer, and a highly safe substance is used as an effective component therein. An antibacterial agent for *Helicobacter pylori* is characterized in that at least one substance selected from the group consisting of ethylenediaminetetraacetic acid and its metal salts is contained as an effective component.

8 Claims, 1 Drawing Sheet

CHELATE COMPOUND-CONTAINING ANTIBACTERIAL AGENT FOR *HELICOBACTER PYLORI*

FIELD OF THE INVENTION

The present invention relates to an antibacterial agent for *Helicobacter pylori*, in more detail, to an antibacterial agent for *Helicobacter pylori*, said agent contains as an effective component achelate compound, safety of which against human bodies is confirmed.

BACKGROUND OF THE INVENTION

Recently, it has been found that *Helicobacter pylori* is much participated to occurrence of chronic gastritis and gastric ulcer. In Japan, it is said that about 60 millions people corresponding to an about half of total populations are infected with *Helicobacter pylori* (Shokunokagaku, Vol. 265, pages 87–99, 2000).

Cure of chronic gastritis and gastric ulcer can be attained by removing the bacterium from stomach by means of administration of antibiotics etc. However, there are some cases wherein the bacterium is hard to be removed depending on patients. Further, as to antibiotics, there are some problems concerning appearance of resistant bacteria and side effects.

Further, it is desirable to remove the bacterium not only on people being attacked with a disease but also on people infected with a disease, but it is economically difficult because the number of objectives is quite large.

Therefore, an antibacterial agent for *Helicobacter pylori* which is highly safe and which can be taken easily is required.

Ethylenediaminetetraacetic acid (hereinafter, sometimes abbreviated to EDTA) has a chelating action on various metal ions and it is known as a reaction inhibitor of enzymes requiring metal ions. Further, EDTA and its metal salts are approved as a food additive in many countries since they have a stabilizing effect for food colors.

Thus, evaluation for safety of EDTA etc. has been already established and an acceptable daily intake (ADI) as a food additive is 2.5 mg/kg of weight (FAO/WHO: Codex Alimentarius Commission, List of additives evaluated for their safety in use in food. CAC/FAL 1-1973, 1973).

Further, in the U.S.A., it is approved that EDTA disodium salt is added to foods within a concentration range of 36–500 ppm (Code of Federal Regulations, Title 21: Food and Drugs, US Government Printing Office, 1988).

SUMMARY OF THE INVENTION

An object of the invention is to provide an antibacterial agent which has an action for growth inhibition of *Helicobacter pylori* which participates to occurrence of chronic gastritis and gastric ulcer and in which a highly safe substance is used as an effective component.

The inventors of the present invention have searched for antibacterial substances for *Helicobacter pylori* among of substances accepted as food additives in order to solve the above-mentioned problem, and found that one kind of a chelating agent, EDTA, and its metal salts. have an action for growth inhibition of *Helicobacter pylori*. Thus, the present invention has been completed based on this finding.

That is, the present invention relates to an antibacterial agent for *Helicobacter pylori*, characterized in that at least one substance selected from ethylenediaminetetraacetic acid and its metal salts is contained as an effective component.

DETAILED DESCRIPTION OF THE INVENTION

Figure 1:
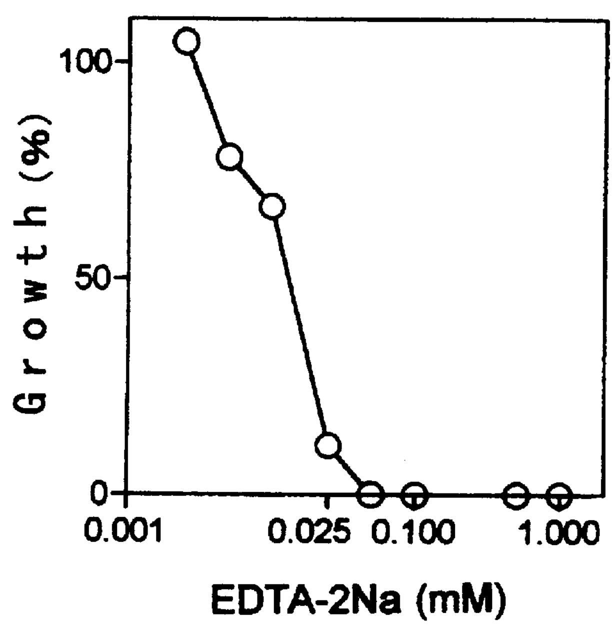
FIG. 1 is a drawing showing growth rates of *Helicobacter pylori* in the presence of disodium ethylenediaminetetraacetate having various concentrations.

According to the invention, at least one substance selected from EDTA and its metal salts is used as an effective component of an antibacterial agent for *Helicobacter pylori*.

As the metal salt of EDTA, any one having an objective antibacterial action may be used. For example, sodium salts, calcium salts and iron salts are preferable. In particular, disodium salt, tetrasodium salt and monocalcium disodium salt of EDTA as well as iron (III)-sodium ethylenediaminetetraacetate are preferable.

The antibacterial agent according to the invention may be adopted to various forms. For example, EDTA or its metal salt may be used alone or in combination of two or more, if necessary with any suitable adjuvant (such as a vehicle, an extender and a sweetening agent), to make any type of an agent such as a powder, a granule, a solution and a capsule. Further, EDTA and its metal salts may be used by adding them to various foods. The antibacterial agent according to the invention is generally administered orally.

Dosages of EDTA and its metal salts may be determined in due consideration of ADI of EDTA, that is, 2.5 mg/kg of weight, as well as these effective amounts for growth inhibition of *Helicobacter pylori* and a stomach volume (about 1.5 L) of human beings.

In order to inhibit growth of *Helicobacter pylori* in stomach, EDTA and/or its metal salt may be administered for an adult per a day at about 10–500 mg, preferably 10–150 mg, calculated as free EDTA. Also, for the case of iron (III)-sodium ethylenediaminetetraacetate, it is suitable to administer for an adult per a day at about 60–300 mg, preferably 60–150 mg. If administered in excess, there may be occurred a side effect. Herein, administration of EDTA etc. may be carried out at a time or may be divided in several times.

The antibacterial agent of the invention maybe used in together with other known antibacterial agents for *Helicobacter pylori*, or also with proton pump inhibitors such as omeprazole or anti-ulcer agents such as bismuth salt.

According to the invention, an antibacterial agent for *Helicobacter pylori* is provided in which highly safe EDTA or its metal salt approved as a food additive in many countries is contained an effective component.

Growth of *Helicobacter pylori* present in a digestive system of human beings can be inhibited effectively by administering the antibacterial agent alone or in together with suitable adjuvants or by taking a food containing it. Thus, according to the invention, gastrointestinal disorders reported to be participated to *Helicobacter pylori* can be prevented and treated effectively.

EXAMPLES

The invention is illustrated as follows with showing the Example, but the invention is not limited thereto.

Example 1

*Helicobacter pylori* (ATCC 43504 strain, purchased from American Type Culture Collection) was cultured with use of a 96-well plate. That is, each 0.1 mL of a medium having a composition of 3% tryptic soy broth (made by Difco), 10% calf serum for tissue culture (made by Wako Pure Chemical) and disodium ethylenediaminetetraacetate (made by Wako Pure Chemical) or iron (III)-sodium ethylenediaminetetraacetate (made by Doj in Molecular Technologies) having various concentrations adjusted to pH 8.0 was poured separately into a 96-well plate. After inoculation of *Helicobacter pylori*, the plate was introduced in a sealed vessel of 2.5 liter volume, into which AnaeroPack-Helico (made by Mitsubishi Gas Chemical), an agent for absorbing oxygen and generating carbon dioxide gas, was also introduced, and cultured for 5 days under an anaerobic condition at 37° C.

Figure 2:
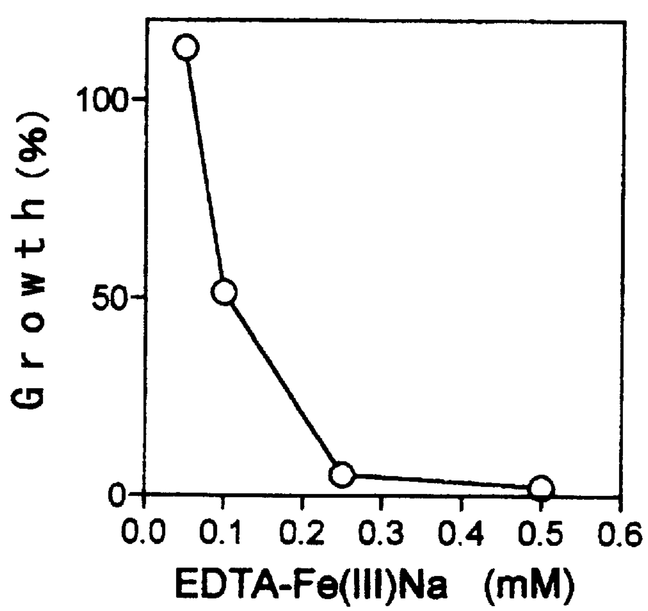
FIG. 2 is a drawing showing growth rates of *Helicobacter pylori* in the presence of iron (III)-sodium ethylenediaminetetraacetate having various concentrations.

Growth of *Helicobacter pylori* was determined by means of a 96-well plate reader with use of a 540 nm or 595 nm filter. Herein, as a control for absorbance determination, a medium without EDTA was used. Results thereof are shown in FIG. 1 and FIG. 2. In the figures, degree of the growth of *Helicobacter pylori* depending on concentration of the effective component like EDTA etc. was measured with turbidity, and is shown with the rate against turbidity in growth of *Helicobacter pylori* in the control medium.

From FIG. 1, it is seen that growth of *Helicobacter pylori* ATCC 43504 strain is inhibited by means of 0.025–1 mM disodium ethylenediaminetetraacetate. Further, from FIG. 2, it is seen that growth of *Helicobacter pylori* ATCC 43504 strain is inhibited by means of 0.1–0.5 mM iron (III)-sodium ethylenediaminetetraacetate.

Herein, 0.025–1 mM disodium ethylenediaminetetraacetate (molecular weight: 372Da) is converted into 9.3–372 mg/L, which is less than 500 ppm, which is, as described above, upper limit of the concentration approved for food additives in the U.S.A.

Further, since a stomach volume of human being is said as about 1.5 L, growth of *Helicobacter pylori* can be inhibited if 14–558 mg (11–438 mg as free EDTA) of disodium ethylenediaminetetraacetate is taken.

On the other hand, for the case of iron (III)-sodium ethylenediaminetetraacetate (molecular weight: 421Da), growth of *Helicobacter pylon* can be inhibited if 63–316 mg is taken.

What is claimed is:

1. A method for treating at least one of chronic gastritis and gastric ulcer in a human in need thereof comprising administering to said human an anti-*Helicobacter pylori* effective amount of at least one substance selected from the group consisting of disodium ethylenediaminetetraacetic acid and iron (III)-sodium ethylenediaminetetraacetate.

2. The method of claim 1, wherein said at least one substance is disodium ethylenediaminetetraacetate.

3. The method of claimed 1, wherein said at least one substance is iron (III)-sodium ethylenediaminetetraacetate.

4. The method of claim 2, wherein the disodium ethylenediaminetetraacetate is in an amount of 0.005 to 1 mM.

5. The method of claim 2, wherein the disodium ethylenediaminetetraacetate is in an amount of 0.005 to 0.1 mM.

6. The method of claim 2, wherein the disodium ethylenediaminetetraacetate is in an amount of 0.025 to 1 mM.

7. The method of claim 2, wherein the disodium ethylenediaminetetraacetate is in an amount of 0.025 to 0.1 mM.

8. The method of claim 3, wherein the iron (III)-sodium ethylenediaminetetraacetate is in an amount of 0.1 to 0.5 mM.

* * * * *